United States Patent
Peretti et al.

(10) Patent No.: US 10,940,236 B2
(45) Date of Patent: Mar. 9, 2021

(54) COMPOSITE SCAFFOLD FOR TISSUE REPAIR

(71) Applicants: OSPEDALE SAN RAFFAELE SRL, Milan (IT); UNIVERSITÀ DEL SALENTO, Lecce (IT)

(72) Inventors: Giuseppe Peretti, Milan (IT); Gianfranco Fraschini, Milan (IT); Alessandro Sannino, Portici (IT); Francesca Gervaso, Lecce (IT); Francesco Scalera, Mesagne (IT); Alessia Di Giancamillo, Milan (IT); Cinzia Domeneghini, Milan (IT); Daniela Rosa Deponti, Lurano (IT)

(73) Assignees: OSPEDALE SAN RAFFAELE S.R.L., Milan (IT); UNIVERSITÀ DEL SALENTO, Lecce (IT)

( * ) Notice: Subject to any disclaimer, the term of this patent is extended or adjusted under 35 U.S.C. 154(b) by 26 days.

(21) Appl. No.: 14/891,932

(22) PCT Filed: May 19, 2014

(86) PCT No.: PCT/EP2014/060264
§ 371 (c)(1),
(2) Date: Nov. 17, 2015

(87) PCT Pub. No.: WO2014/184391
PCT Pub. Date: Nov. 20, 2014

(65) Prior Publication Data
US 2016/0106885 A1    Apr. 21, 2016

Related U.S. Application Data

(60) Provisional application No. 61/824,706, filed on May 17, 2013.

(51) Int. Cl.
| | |
|---|---|
| A61L 27/24 | (2006.01) |
| A61L 27/12 | (2006.01) |
| A61L 27/38 | (2006.01) |
| A61L 27/54 | (2006.01) |
| A61L 27/56 | (2006.01) |
| A61L 27/06 | (2006.01) |
| A61L 27/16 | (2006.01) |

(52) U.S. Cl.
CPC ............ *A61L 27/24* (2013.01); *A61L 27/06* (2013.01); *A61L 27/12* (2013.01); *A61L 27/16* (2013.01); *A61L 27/3817* (2013.01); *A61L 27/3852* (2013.01); *A61L 27/54* (2013.01); *A61L 27/56* (2013.01); *A61L 2300/414* (2013.01); *A61L 2300/64* (2013.01); *A61L 2430/02* (2013.01); *A61L 2430/06* (2013.01)

(58) Field of Classification Search
None
See application file for complete search history.

(56) References Cited

U.S. PATENT DOCUMENTS

2012/0015003 A1    1/2012    Gleeson et al.

FOREIGN PATENT DOCUMENTS

JP        2007159935 A      6/2007

OTHER PUBLICATIONS

Kikuchi et al (English machine translation of JP2007159935A published on Jun. 28, 2007 (20 pages)) (Year: 2007).*
English translation of JP2007159935A to Kikuchi et al (pp. 1-42 (43 total pages)) (Year: 2007).*
Hua-ding Lu et al., "Construction of tissue engineering cartilage with collagen/hydroxyapatite compsite scaffolds loaded chondrocytes in vitro," Chinese Journal of Clinical Rehabilitation, Zhongguo Kangfu Yixuehui, CN, vol. 10, No. 25, Jul. 10, 2006, pp. 177-180.
PCT International Search Report and Written Opinion issued in corresponding PCT Application No. PCT/EP2014/060624, dated Jun. 26, 2014 (12 pages).

* cited by examiner

*Primary Examiner* — Dennis J Parad
(74) *Attorney, Agent, or Firm* — Lucas & Mercanti, LLP

(57) ABSTRACT

A synthetic composite material for tissue repair is disclosed which includes a first layer having an organic material and having side walls and external surface; and a second porous layer comprising an inorganic material and having side walls; wherein the first layer is in direct contact with the second layer and wherein the side walls of the first layer and the side walls of the second layer are coated with a third layer of the organic material.

18 Claims, 13 Drawing Sheets

A 1° SURGERY

B CHONDROCYTE ISOLATION, EXPANSION AND SEEDING

C 2° SURGERY

A

*Mold A – Lyo 1*

*Mold B – Lyo 2*

B

*Mold A – Lyo 1*

*Mold B – Lyo 2*

C

D

E

COMPOSITE SCAFFOLD FOR TISSUE REPAIR

CROSS-REFERENCE TO RELATED APPLICATIONS

Figure 1:
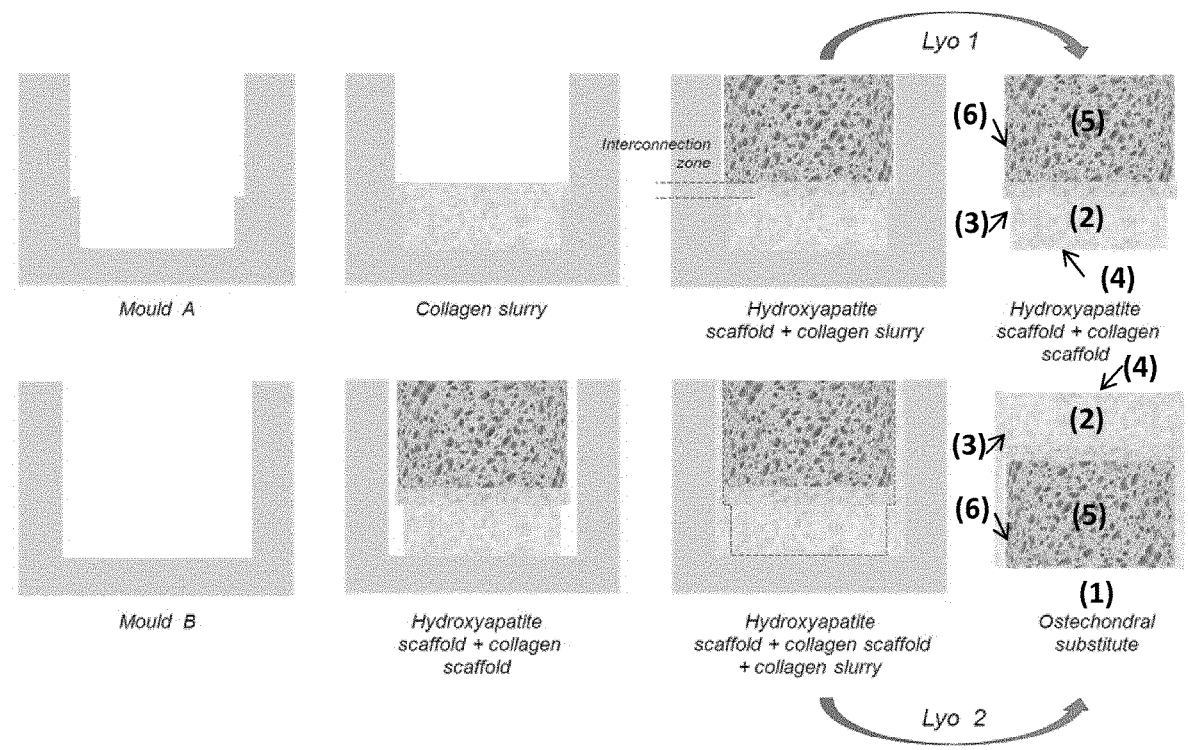

This application is a 371 of PCT/EP2014/060264, filed May 19, 2014, which claims the benefit of U.S. Provisional Patent Application No. 61/824,706, filed May 17, 2013.

TECHNICAL FIELD

The present invention relates to a synthetic composite material comprising a first layer comprising an organic material and a second porous layer comprising an inorganic material wherein said first layer is in direct contact with said second layer and wherein the side walls of the first layer and the side walls of the second layer are coated with a layer of the organic material, use and preparation thereof.

BACKGROUND ART

In the natural joint, articular cartilage and subchondral bone form the load-bearing system that provides a large range of joint motion with excellent lubrication, stability and uniform distribution of high acting loads [1-3]. Very often, articular cartilage and subchondral bone undergoes degeneration as the result of traumas, osteoarthritis and related disorders [4-6], leading to severe pain, joint deformity and loss of joint motion [7] thus requiring surgical procedures for treatment of osteochondral defects. The origin of the cartilage and subchondral bone degradation is often unknown. One of the scenarios could be that the subchondral bone becomes weaker [8-10] and unable to support cartilage in transmitting loads to the cancellous and cortical bones. As a result, cartilage fractures arise. Great debate still persists about the best available treatment for symptomatic osteochondral defects. Traditional treatment methods includes debridement, drilling [11] and microfracture [12] that aim, by the further violation of subchondral bone, at bringing blood elements into the defect site. Although the cells provided by the bone marrow should differentiate into cartilage, fibrous tissue represents predominant tissue type that usually forms using these procedures. However, fibrous tissue or fibrocartilage do not exhibit the wear characteristics of hyaline cartilage. Another currently used surgical technique is the mosaicplasty [13], consisting in filling the debrided lesion by biological autografts. However, this procedure is strongly limited by the insufficient supply of donor tissue and by the difficulty of carving the host tissue into the desired three-dimensional shape. In the recent years, the application of the tissue engineering approaches to the repairing osteochondral defects has received an increasing interest. However, because of the extremely different nature of cartilage and bone, when a mono-phasic scaffold is used [14,15] the natural environment is not well duplicated and the new tissue is not properly formed. For such purpose, modern approaches focus on the design and development of scaffolds combining distinct layers mimicking the natural cartilage and bone tissues. In literature, several bi- or three-layered ostechondral scaffolds made of different materials are described. The soft part, mimicking the cartilage, is usually collagen while the bottom part, mimicking the subchondral bone, is prevalently hydroxyapatite (HA) [16-18]. Some studies reported results on bi-layered in which, instead of the collagen, chitosan [19], PLGA [20], PVA [21] were used. In the authors' study, a novel three-dimensional collagen/hydroxyapatite ostechondral substitute is proposed. The document WO2006095154 refers to a process for the preparation of a composite biomaterial comprising an inorganic material and an organic material, the process comprising providing a first slurry composition comprising a liquid carrier, an inorganic material and an organic material; providing a mould for the slurry; depositing the slurry in the mould; cooling the slurry deposited in the mould to a temperature at which the liquid carrier transforms into a plurality of solid crystals or particles; removing at least some of the plurality of solid crystals or particles by sublimation and/or evaporation to leave a porous composite material comprising an inorganic material and an organic material; and removing the material from the mould. The document also discloses a synthetic composite biomaterial, wherein at least part of the biomaterial is formed from a porous co-precipitate comprising a calcium phosphate material and one of collagen (including recombinant human (rh) collagen), a glycosaminoglycan, albumin, hyaluronan, chitosan or a synthetic polypeptides comprising a portion of the polypeptide sequence of collagen, wherein the macropore size range (pore diameter) is preferably from 1-1000 microns, more preferably from 200-600 microns.

The patent application WO03094703 relates to a transplantable osteochondral implant and a method for its production. The transplantable osteochondral implant comprising engineered cartilage tissue attached to a biocompatible support scaffold comprising a plurality of pores, wherein the cartilage tissue is derived from chondrogenic cells cultured in vitro, the cells having a cell associated matrix (CM), and wherein the scaffold is selected from the group consisting of at least one of natural cancellous bone, demineralized natural cancellous bone, collagen, and bone substitute material. WO2008157608 refers to a porous multi-layer composite scaffold useful for tissue regeneration and a method of fabricating the same. The porous multi-layer composite scaffold comprises a first layer comprising crosslinked collagen and a polysaccharide; a second layer of crosslinked collagen and calcium based minerals, which is covalently bonded to the first layer; and a third layer of crosslinked collagen and a polysaccharide, which is covalently bonded to the second layer. Preferably, the second layer further comprises a polysaccharide. The ratio of collagen to polysaccharide in each of the three layers is from about 3:1 to about 1:1 by weight. The porous multi-layer composite scaffold may further comprises a biologically active agent. WO2011107807 refers to a process for fabricating a biomaterial, comprising joining a porous collagen based-material with a non-porous collagen based-material by applying a controlled amount of a bonding layer of a gel comprising collagen to a bonding surface of the non-porous collagen based-material, and contacting a surface of the porous collagen based-material with the gel applied to the bonding surface to partially hydrate a section of the porous material at the interface between the materials. The application also relates to a fabricated biomaterial comprising porous and non-porous collagen-based materials bonded with a bonding layer of dried gel comprising collagen, wherein the collagens in the bonding layer are cross-linked. The publication Gervaso et al. (Key Engineering Materials Vols. 493-494 (2012) pp 890-895) [22] refers to a three-dimensional ostechondral substitute made of an inorganic/organic hybrid material, namely collagen/hydroxyapatite. The two components of the substitute have been characterized separately. The inorganic part, a hydroxyapatite scaffold, was fabricated by a polymer sponge templating method using a reactive sub-micron powder synthesized by hydroxide precipitation sol-gel route. The organic part, a collagen scaffold, was fabricated by a freeze-dying technique varying design parameters. The collagen scaffolds were seeded with chondrocytes, processed for histological analysis and tested in compression. However, there is still the need for a whole osteochondral substitute that guarantees the perfect integration between the various layers or scaffolds in order to be successfully implanted for tissue repair.

SUMMARY OF THE INVENTION

In the present invention, the potential of a novel three-dimensional composite substitute for repairing soft or hard tissue lesions, in particular osteochondral lesions, in a swine model was evaluated. In particular, osteochondral lesions were treated with chondrocytes-seeded scaffolds or with unseeded osteochondral material and compared also to untreated lesions.

A three-dimensional biphasic substitute that is made of an organic/inorganic hybrid material is proposed for the repair of osteochondral lesion. The organic part, a collagen scaffold, is a collagen type 1 sponge, previously characterized for its compatibility and application in vitro and vivo as supporting material for engineering cartilage. The inorganic part, a hydroxyapatite (HA) scaffold, is fabricated by a polymer sponge templating method using a reactive sub-micron powder synthesized in the authors' laboratory by hydroxide precipitation sol-gel route. The whole osteochondral substitute is fabricated by a method that guarantees the perfect integration between the two scaffolds. The substitutes were produced in the suitable dimensions for the in vivo test and successfully implanted in osteochondral lesions of swine knees. Thirty-six osteochondral lesions were created in the trochlea of 6 pigs (6 lesions for pig); in each pig two scaffolds with autologous chondrocytes and two scaffolds unseeded were implanted, while the other two lesions were left untreated. After three months, the animals were sacrificed and the composites were removed and characterized to evaluate the degree of maturation of the repaired tissue. The gross repair assessment of specimens, evaluated by ICRS Macroscopic Score, was nearly normal (grade 2) only for the untreated group while for the lesions treated with seeded or unseeded scaffold the repair assessment was abnormal (grade 3). Microscopic evaluation (ICRS Visual Histological Assessment Scale II) showed significant higher scores for chondrocytes morphology and the superficial layer recovery in the unseeded scaffolds group, with respect to the seeded scaffold group and the untreated lesions; while the immunohistochemical analysis showed an increasing immunopositivity to the collagen type 2 from the superficial to the deep level of the chondral defect in the seeded scaffold group. Biochemical evaluation showed a significant higher cellularity in seeded scaffold group while the GAGs (glycosaminoglycans)/DNA ratio was higher in the untreated lesions with respect to the seeded and unseeded scaffolds. The present invention showed that the scaffold was easy to handle for surgical implant and stable in the site of implant; at the end of experimental time no signs of synovitis were revealed and all implants were well integrated to the surrounding tissue. The quality of the repaired tissue is superior in the lesions treated with the unseeded scaffolds, thus it is a promising biomaterial. The present scaffold displays various advantages: the scaffold is more rigid and has an increased compactness and biomechanical integrity with respect to commercially available scaffold (Maioregen). It is then useful for early physiotherapy and is able to better withstand weight. Further, the components (collagen/HA) are better kept together and are less likely to peel off. The external walls of collagen that wrap the HA portion of the scaffold allow a press fit more simple and the entry of chondrocytes in the scaffold. In addition, the scaffold can be better handled by the medical staff when implanted. Moreover, the scaffolds may be "tailor-made" and personalized.

DETAILED DESCRIPTION OF THE INVENTION

It is therefore an object of the present invention a synthetic composite material (1) for tissue repair comprising:
a first layer (2) comprising an organic material and having side walls (3) and external surface (4);
a second porous layer (5) comprising an inorganic material and having side walls (6); wherein said first layer is in direct contact with said second layer and wherein the side walls (3) of the first layer and the side walls (6) of the second layer are coated with a third layer comprising the organic material.

In a preferred embodiment, the synthetic composite material according the invention further comprises an interconnection zone between the first layer and the second layer wherein the organic material and the inorganic material are co-present.

Preferably, in the synthetic composite material according to the invention the first layer is 0.1-20 mm high and/or the second layer is 2-400 mm and/or the third layer is 0.1-2 mm high and/or the interconnection zone is 0.5-3 mm high, preferably 1 mm high.

In a preferred aspect, the organic material is selected from the group consisting of: at least one collagen and/or any derivative thereof, chondroitin-sulphate, hyaluronic acid and derivatives thereof, polyglactin, polydioxanone, alginate, agarose, chitosan and derivatives thereof, fibrin glue, polyethylene glycol diacrylate or a combination thereof. Still preferably the first layer comprises from 0.5 wt % to 5 wt % of organic material. Still preferably the inorganic material is selected from the group consisting of at least: hydroxyapatite, calcium sulphate, calcium silicate, calcium phosphate, magnesium silicate, metal, preferably magnesium or titanium, Poly(D,L-lactide-co-glycolide) or a combination thereof. In a preferred embodiment the second layer comprises from 50 wt % to 80 wt % of inorganic material. In a still preferred embodiment the second porous layer has a pore dimension between 50 μm and 700 μm.

In the synthetic composite material according to the invention, the organic material of the first layer is preferably complexed with at least one polyanionic substance, wherein the polyanionic substance is preferably a signaling molecule, more preferably a growth factor, even more preferably a growth factor selected from the group consisting of: transforming growth factor-β1 (TGF-β1), bone morphogenetic proteins (BMPs) and insulin growth factor-1 (IGF-1). In a preferred embodiment, the organic material complexed with the above polyanionic substance is chitosan.

In a still preferred embodiment the first layer (2) is seeded with cells, which may penetrate within the full thickness of the first layer. Preferably the cells are chondrocytes.

A further object of the invention is a process for the preparation of the synthetic composite material as above disclosed.

It is a further object of the invention a process for the preparation of a synthetic composite material comprising a first layer comprising an organic material and a second layer comprising an inorganic material comprising the steps of:

a) pouring in a first mould a slurry composition comprising a liquid carrier and an organic material;
b) inserting in the mould an inorganic material;
c) performing a freeze-dry cycle;
d) inducing dehydrothermal crosslinking to obtain an intermediate material;
e) removing the intermediate material from the first mould;
f) introducing at least one intermediate material in a second mould characterized by having an internal area larger than the first mould;
g) pouring the slurry composition comprising the liquid carrier and the organic material until the mould is filled;
h) performing a freeze-dry cycle;
i) inducing dehydrothermal crosslinking and
j) optionally sterilizing the material.

In the present invention the intermediate material obtained in step d) is also defined as a bi-layer scaffold. The first mould of step a) may herein also be defined as MOLD A and the second mould of step f) may herein also be defined as MOLD B.

In a preferred aspect, the number of the intermediate material produced as above defined that has to be introduced in the second mould of step f) goes from 1 to 18 in a volume of 1 cc.

In a preferred aspect the first mould may allow to obtain an intermediate material having a transversal section of a circle, square, polygon or any closed polyline. Preferably, the organic material is selected from the group consisting of: at least one collagen and/or any derivative thereof, chondroitin-sulphate, hyaluronic acid and derivatives thereof, polyglactin, polydioxanone, alginate, agarose, chitosan and derivatives thereof, fibrin glue, polyethylene glycol diacrylate or a combination thereof. The first layer preferably comprises from 0.5 wt % to 5 wt % of organic material. The inorganic material is preferably selected from the group of: hydroxyapathite, calcium sulfate, calcium silicate, calcium phosphate, magnesium silicate, a metal, preferably magnesium or titanium, Poly(D,L-lactide-co-glycolide) or a combination thereof. The second layer preferably comprises from 50 wt % to 80 wt % of inorganic material and/or has a pore dimension between 50 μm and 700 μm. Preferably, the organic material of the first layer is complexed with at least one polyanionic substance, wherein the polyanionic substance is preferably a signaling molecule, more preferably a growth factor, even more preferably a growth factor selected from the group consisting of: transforming growth factor-β1 (TGF-β1), bone morphogenetic proteins (BMPs) and insulin growth factor-1 (IGF-1).

Yet preferably dehydrothermal cross linking is carried out in an oven at a temperature between 110° C. and 130° C. under vacuum for between 48 and 96 hours.

In a preferred embodiment the inorganic material is obtainable by:
impregnating a porous support with a slurry comprising 50-80 wt % of inorganic material;
drying and heating the material in order to eliminate the porous support;
sintering.

Preferably sintering occurs at a temperature between 500° C. and 1500° C., more preferably 500° C. and 700° C. or 1200° C. and 1350° C. For examples, for metals a preferred range of temperature is 500° C.-700° C., while for HA a preferred range of temperature is 1200° C.-1350° C.

Preferably the process further comprises seeding the first layer with cells. Preferably the cells are chondrocytes. Preferably, the synthetic composite material obtainable according to the above process further comprises a third layer comprising the organic material coating the side walls of the first layer and the side walls of the second layer and/or further comprises an interconnection zone between the first layer and the second layer wherein the organic material and the inorganic material are co-present. In the synthetic composite material obtainable according to the above process the first layer is preferably 0.1-20 mm high and/or the second layer is preferably 2-400 mm and/or the third layer is preferably 0.1-2 mm high and/or the interconnection zone is preferably 0.5-3 mm high, more preferably 1 mm high.

It is a further object of the invention a synthetic composite material obtainable according to the process as defined above.

Preferably, in the synthetic composite material as above disclosed the second layer has a transversal section of a circle, a square, a polygon or any closed polyline. Preferably, in the synthetic composite material as above disclosed the first layer has a transversal section of a circle, a square, a polygon or any closed polyline.

In the process of the invention, the inorganic material inserted in the mould in step b) and/or the intermediate material of step d) has preferably a transversal section of a circle, a square, a polygon or any closed polyline.

In the above process, when two or more intermediate materials are introduced in the second mould of step f), the obtainable synthetic composite may be defined as a composite structure.

A further object of the invention is a composite structure comprising one or more synthetic composite material as defined above. Preferably, the composite structure comprises at least two synthetic composite materials or intermediate materials as defined above. The composite structure will result made of different percentage of volume occupied by the inorganic material, occupied by organic material and of volume occupied by both inorganic and organic material (compenetration between). A preferred percentage is: 19% inorganic, 72% organic, 9% co-presence of both (compenetration). The composite structure may comprise one or more layer of synthetic composite material or intermediate materials as above defined, and the synthetic composite material or intermediate materials may be of different dimensions and shape (circle and squared section e.g.).

Another object of the invention is the synthetic composite material as above defined, or the composite structure as above defined for use in a method of tissue engineering, preferably cartilage tissue engineering. In particular, tissue engineering comprises e.g. the treatment of osteochondral or skin defects or lesions. Preferably the tissue is soft or hard tissue.

It is a further object of the invention a synthetic bone material, bone implant, bone graft, bone substitute, bone scaffold, filler, coating or cement comprising the synthetic composite material as defined above or the composite structure defined above.

Another object of the invention is a synthetic skin material, plaster, bandage comprising the synthetic composite material as above defined, or the composite structure as above defined.

A further object of the invention is a method of treatment of osteochondral defects comprising implanting in a subject in need thereof the synthetic composite material as above defined, or the composite structure as above defined. Another object of the invention is a method of treatment of skin defects comprising applying on a subject's skin in need thereof the synthetic composite material as above defined, or the composite structure as above defined. Preferably, the first layer comprising an organic material is porous. In a preferred embodiment, the organic material is collagen type 1 and the inorganic material is hydroxyapatite. Alternatively, other types of natural organic polymer may be employed, as for example, collagen type 2, collagen type 3 or chitosan. Chitosan, is a natural polysaccharide that is structurally similar to GAGs and has recently emerged as an alternative material for cartilage tissue engineering. Chitosan shows good biocompatibility, biodegradability and capacity to stimulate the activity of growth factors. In addition, it is known to contribute to the maintenance of the chondrogenic phenotype, especially in terms of its morphology. One of the interesting features of chitosan is its cationic nature occurring from primary amine groups, thus providing a high charge density in an acidic solution. The cationic charges allow chitosan to form water-insoluble ionic complexes with variety of polyanionic substances: e.g. for drug delivery applications. Therefore, the opportunity of the scaffolds to carry and provide signaling molecules, such as growth factors, to the site of implantation is of great interest as it could compensate or potentiate some of the parameters necessary to achieve the desired tissue formation. Growth factors are proteins involved in the cellular communication system which modulate cell activity in a concentration and time dependent fashion. Hundreds of growth factors have been identified that inhibit or stimulate proliferation, differentiation, migration or gene expression of various cell types. With regard to cartilage, several growth factors have regulatory effects on cartilage metabolism among which the most investigated are transforming growth factor-$\beta$1 (TGF-$\beta$1), bone morphogenetic proteins (BMPs) and insulin growth factor-1 (IGF-1). These molecules play a role in the maintenance of the chondrogenic phenotype, the proliferation of chondrocytes and the differentiation of pluripotent progenitor cells towards cartilage. Accordingly, they are promising candidates to be associated with scaffolds to support, induce or enhance the growth and differentiation of different cells types towards the chondrogenic lineage and to guide cartilage repair. To exert their action, each growth factor requires different dosages and length of exposure to the cells. Consequently, they can potentially induce undesired side effects when presented in wrong fashion and if present at systemic levels. Therefore, scaffolds associated with growth factors should provide the means to precisely control their doses and supplementation rate at a local level. In addition, growth factors are labile and have a short half-life in the body. These different characteristics and requirements logically lead to the development of controlled release approaches for the delivery of growth factors from scaffolds. By offering a sustained release of the growth factor to the site of implantation, one can expect to induce a longer and more stable tissue response. The skilled man is able to provide composite materials according to the invention which can deliver growth factors with a controlled release approach. Although the scaffold tested in the present in vivo experiment was made of a single "osseous" inorganic part, i.e. the macroporous HA scaffold (FIG. 10A), the present invention allows to provide more complex systems. After the first freeze-drying in the MOLD A, which allows to get the desired compenetration of the two different components (porous organic and porous inorganic scaffolds) a desired number of the obtained bi-layer scaffolds can be inserted in the MOLD B in order to get a composite structure with an increased compliance in transversal and/or longitudinal direction (FIG. 10B,C). The bi-layer scaffold that can be produced with MOLD A can be of different shape. The transversal section can be a circle, square, polygon or any closed polyline (FIG. 10D). The number of the bi-layer scaffolds produced with MOLD A and that has to be inserted in MOLD B can be variable: from 1 to 18 in a volume of 1 cc. The final complex scaffold made of a variable number of bi-layer scaffold, herein referred also as composite structure comprising one or more synthetic composite material of the invention, can also be of different shape, even custom-made from clinical image of the defect to be repaired. The final complex scaffold will result made of different percentage of volume occupied by the inorganic scaffold, occupied by organic scaffold and of volume occupied by both inorganic and organic scaffold (compenetration between). A preferred percentage is: 19% inorganic, 72% organic, 9% co-presence of both (compenetration). In the table I, an example of the volume % of the inorganic and organic part that it is possible to obtain with different number of bi-layer scaffolds. More in details, for the examples reported in Table I five different assembled configurations of composite scaffolds as shown in FIG. 10E have been considered.

TABLE I

| Number of bi-layer scaffolds | % Inorganic | % Organic | % Inorganic-Organic |
|---|---|---|---|
| 1 | 36% | 46% | 18% |
| 2 | 34% | 49% | 17% |
| 3 | 32% | 53% | 16% |
| 6 | 25% | 62% | 13% |
| 12 | 22% | 67% | 11% |
| GOLD STANDARD - 18 | 19% | 72% | 9% |

The composite structure comprising one or more synthetic composite as above described presents a greater flexibility and an increased cell repopulation in vivo.

The invention will now be illustrated by means of non-limiting examples in reference to the following figures.

FIG. 1: A schematic representation of the procedure for the osteochondral substitute fabrication (see text).

Figure 2:
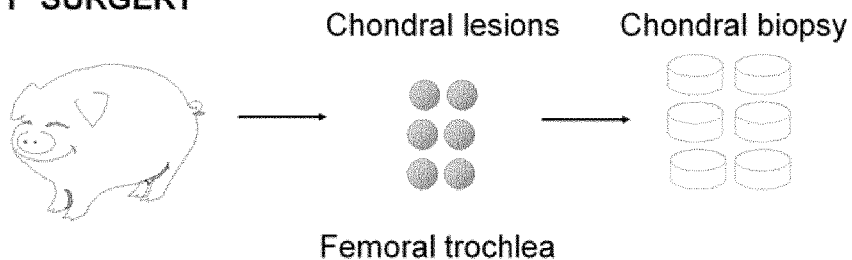
Figure 2:
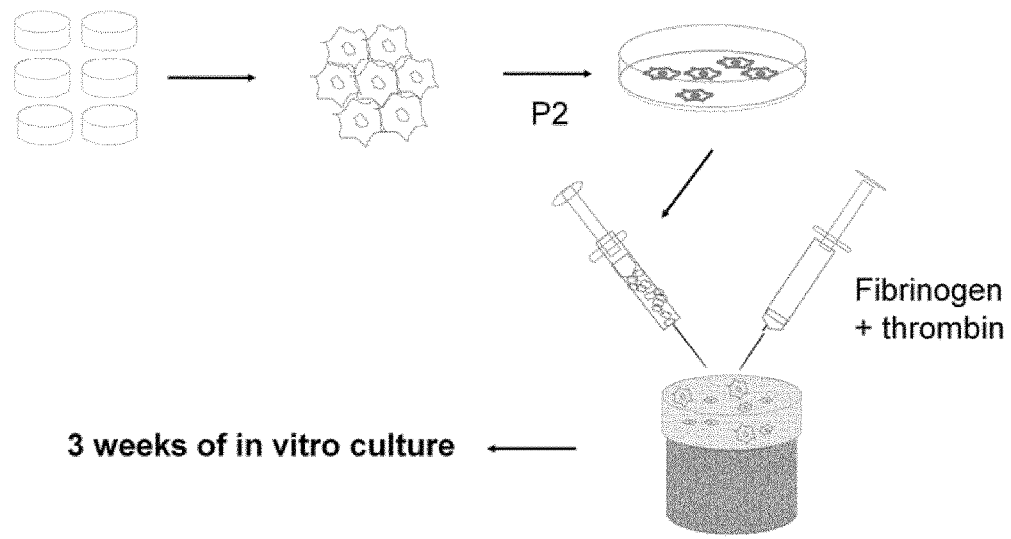
Figure 2:
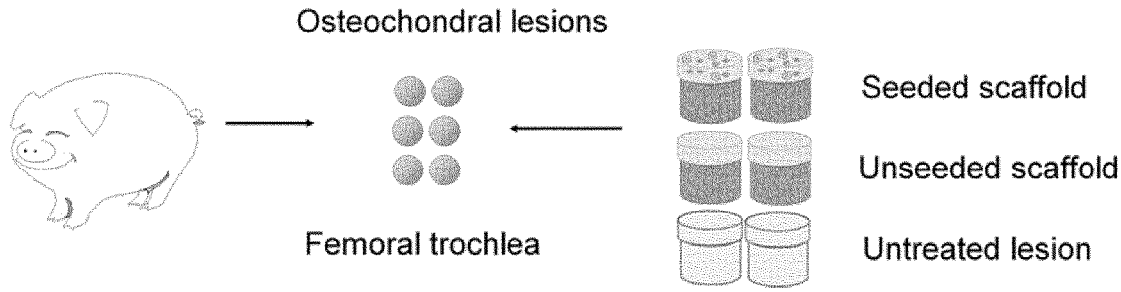

FIG. 2: A) Six chondral lesions were done in the right trochlea of six pigs. B) The 6 chondral biopsies were digested and the autologous chondrocytes were isolated; then the cells were expanded in culture and finally seeded in the collagenic portion of the osteochondral substitute; the seeded substitutes were cultured in chondrogenic medium for 3 weeks and then implanted. C) With a second surgery, the repairing tissue formed in the six lesions was removed generating an osteochondral lesion having the same dimensions of the scaffold; each animal received 2 seeded scaffolds, 2 unseeded scaffolds, while 2 lesions were left untreated.

Figure 3:
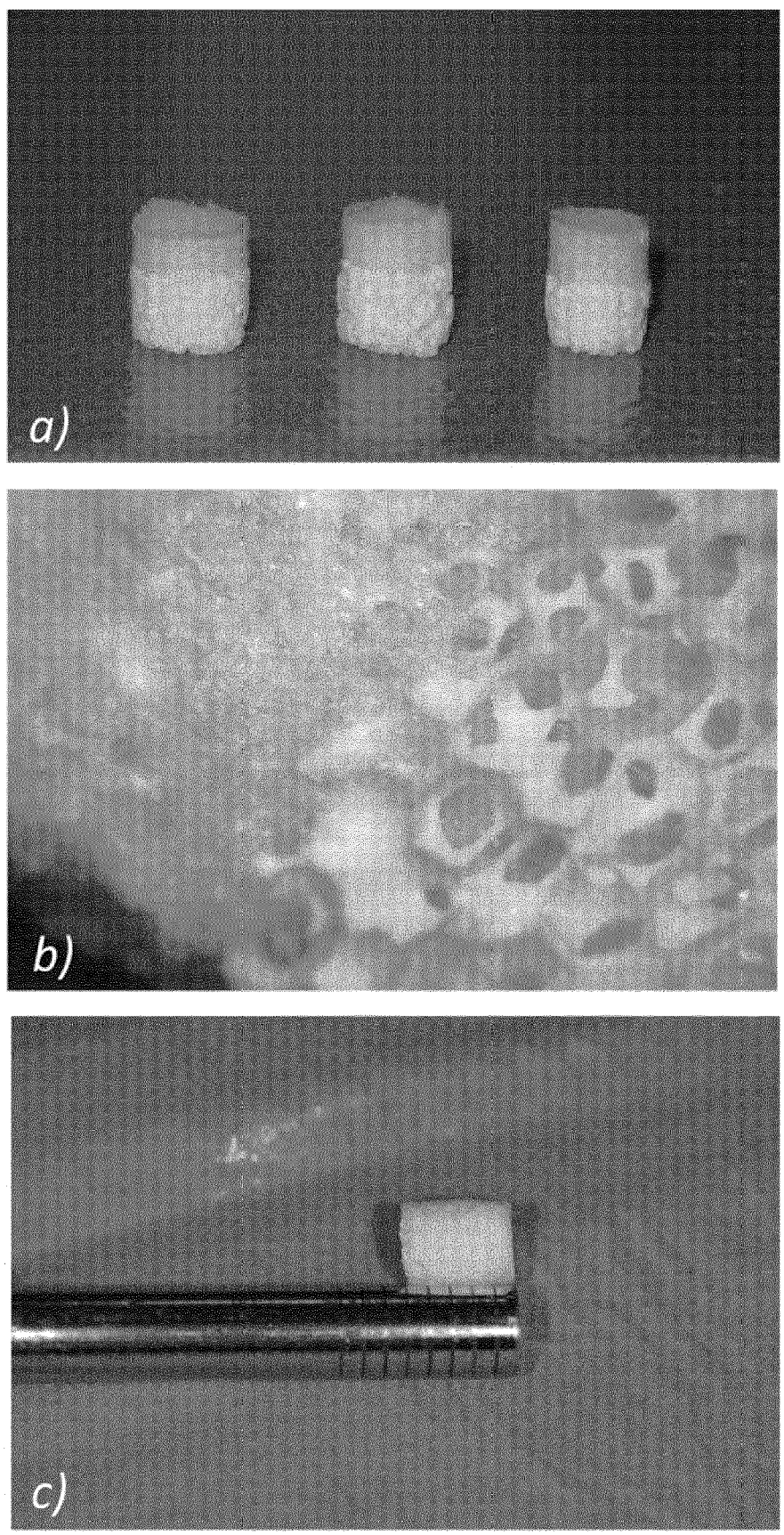

FIG. 3: Characteristics of the bilayered scaffold. (a) Three bilayered scaffolds after first lyophilisation Lyo 1; (b) integration between the collagen and the hydroxyapatite layers; (c) a scaffold at the end of the fabrication process (Lyo 2) before the implantation in the animal.

Figure 4:
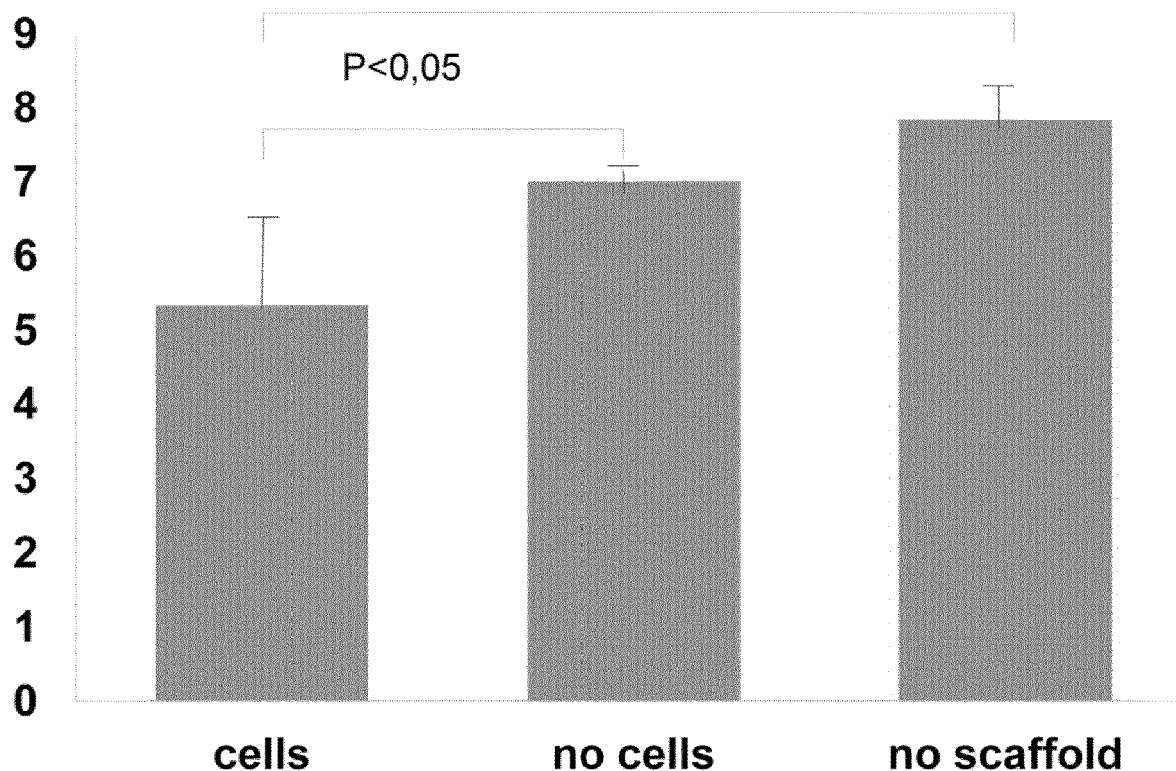

FIG. 4: ICRS Macroscopic Score that showed significant differences among the untreated group (no scaffold) and the groups with scaffolds seeded (cells) and unseeded (no cells). In particular, values were significantly lower in the seeded scaffold with respect to the untreated group and the unseeded scaffold group, suggesting the lack of benefit of the use of cells seeded in the scaffold in facilitating the healing process.

Figure 5:
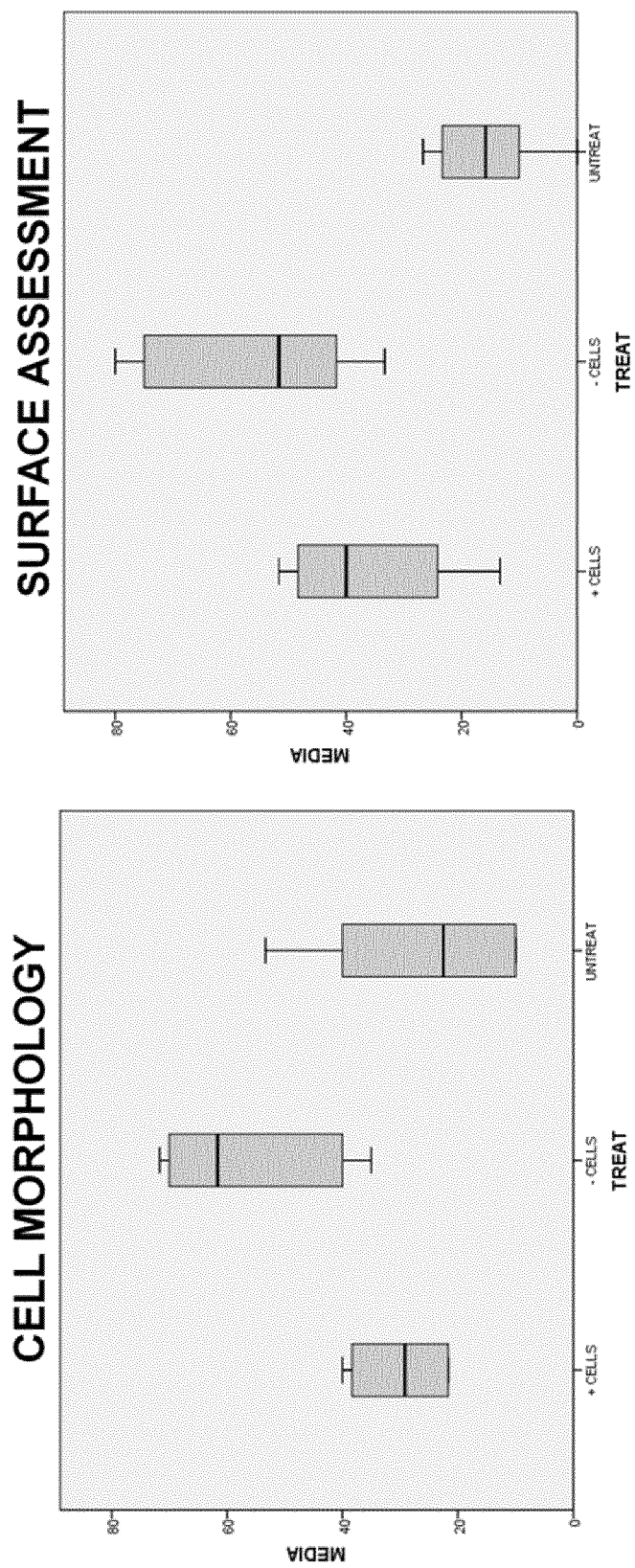

FIG. 5: ICRS II parameters (cell morphology and surface assessment) that showed significant differences among the three experimental groups (Untreated lesion (untreat); Unseeded scaffold (−cells) and Seeded scaffold (+cells). In particular, values were significantly higher in the unseeded scaffold group with respect to the seeded one and the untreated group, suggesting a more efficient repair in the lesions treated with the scaffold alone.

Figure 6:
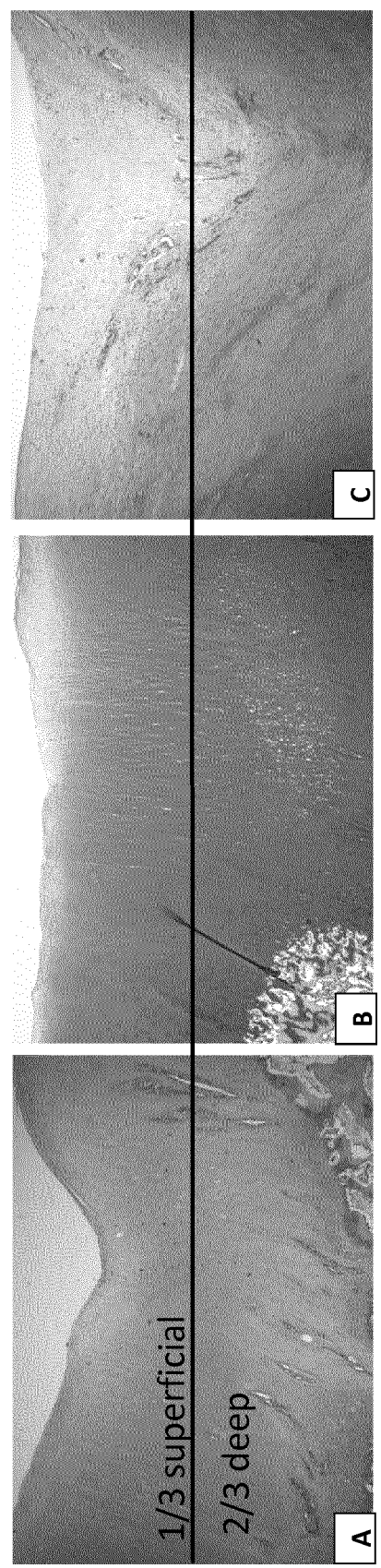

FIG. 6: SAFRANIN-0 staining of the repaired lesion: A) Untreated lesion; B) Unseeded scaffold; C) Seeded scaffold in the 1/3 superficial and 2/3 deep zones.

Figure 7:
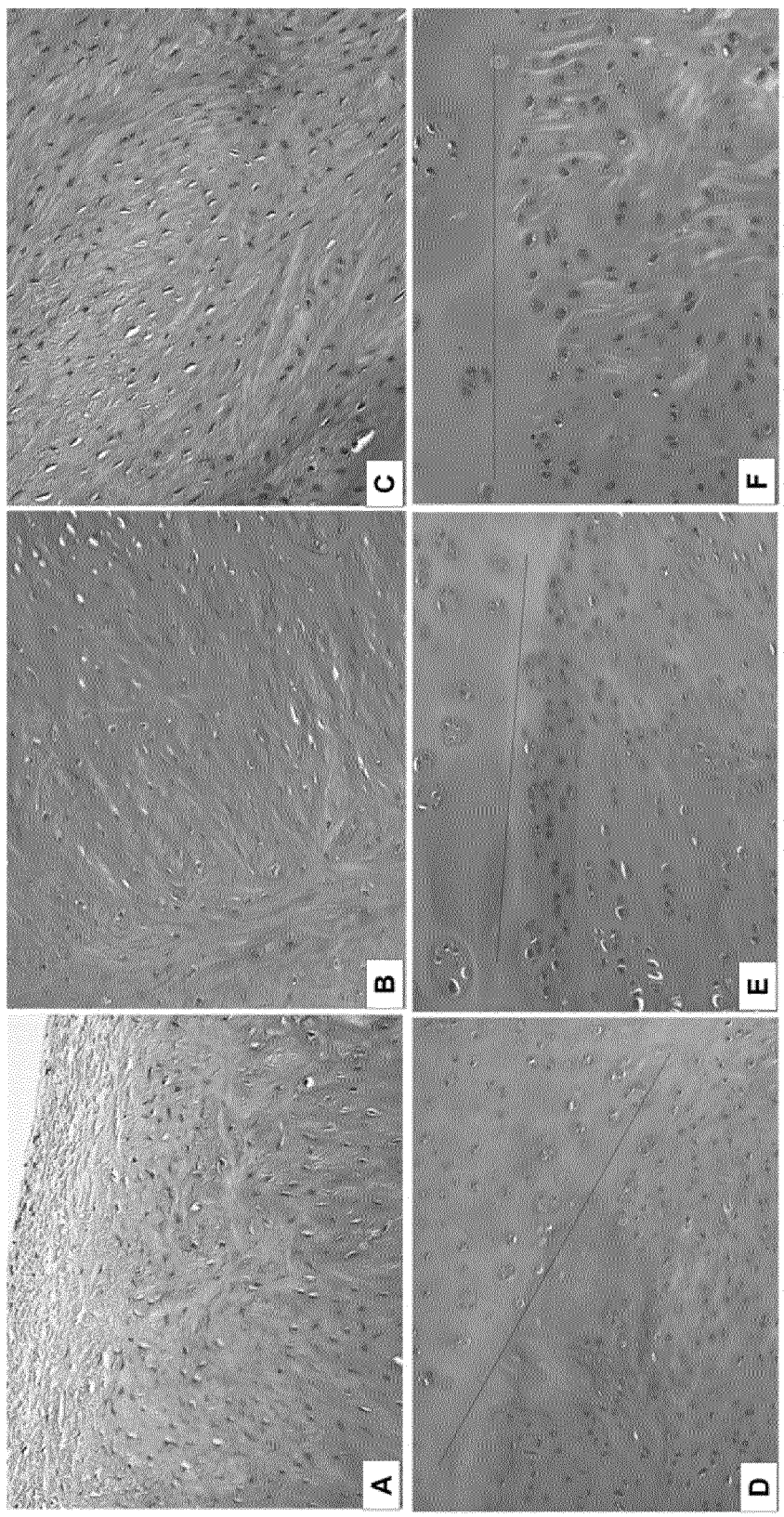

FIG. 7: SAFRANIN-0 staining of the repaired lesion: A,D) Untreated lesion; B,E) Unseeded scaffold; C,F) Seeded scaffold. A-C: Superficial zone; D-F: Deep zone.

Figure 8:
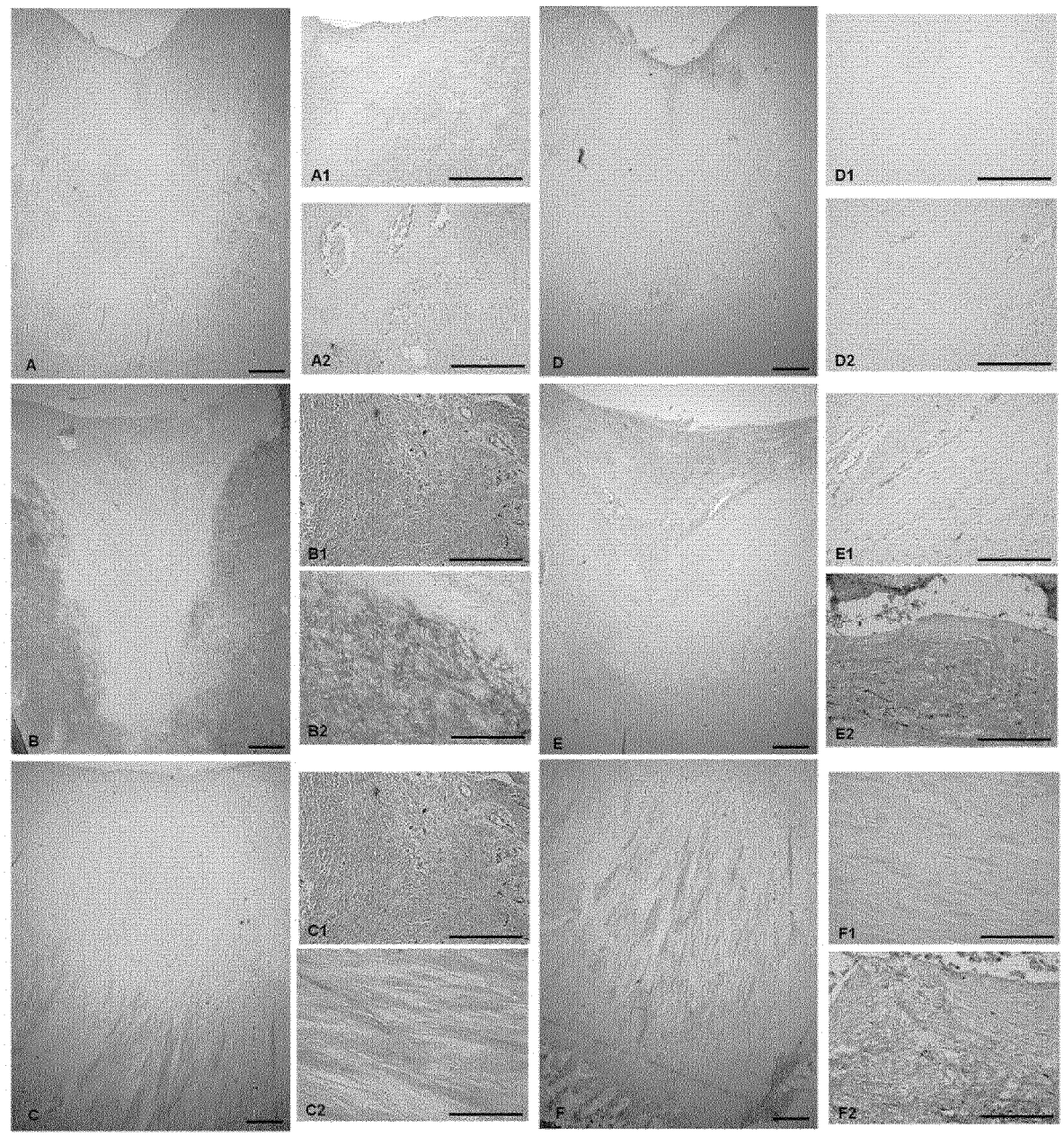

FIG. 8: Collagen 2 (A, B, C) and 1 (D, E, F) immunohistochemical staining of osteochondral defects. All figures have the same scale bar of 200 μm. Collagen type 2. A) Untreated group; scarce immunoreactivity to collagen type 2 in the central zone of the critical defect; A1) immunonegative reactivity in the central area of the defect, where blood vessels are also present; A2) immunonegative reactivity in the deep area where the bone remodeling area is present. B) Scaffold group: scarce immunopositivity in the central zone of the defect, but a high reactivity to collagen 2 in the lateral part of the osteochondral defect is well evident; B1) scarce immunopositivity at a superficial level, with clear fiber fragmentation; B2) strong lateral immunopositivity. C) Scaffold+cells group: an increasing immunopositivity from the superficial to the deep level of the chondral defect is evident; C1) scarce immunopositivity at the superficial level of the chondral defect; C2) strong immunopositivity at a deep level of the chondral defect. Collagen type 1. D) Untreated group: immunonegative reaction to collagen 1 in the whole zone of the osteochondral defect; D1) immunonegative reaction at a superficial level; D2) immunonegative reaction in the area of bone regeneration, where the fibers appear to be fragmented. E) Scaffold group: scarce immunopositivity in the surgical defect area; E1) the distribution of immunopositive bundle fibers is evident; E2) strong immunoreactivity in the area of bone regeneration. F) Scaffold+cells group: very scarce immunoreactivity to collagen 1 at a superficial level; F1) the immunoreacitvity becomes stronger when it comes to a deep level of the defect; F2) immunoreactive fiber bundles in the area of bone regeneration.

Figure 9:
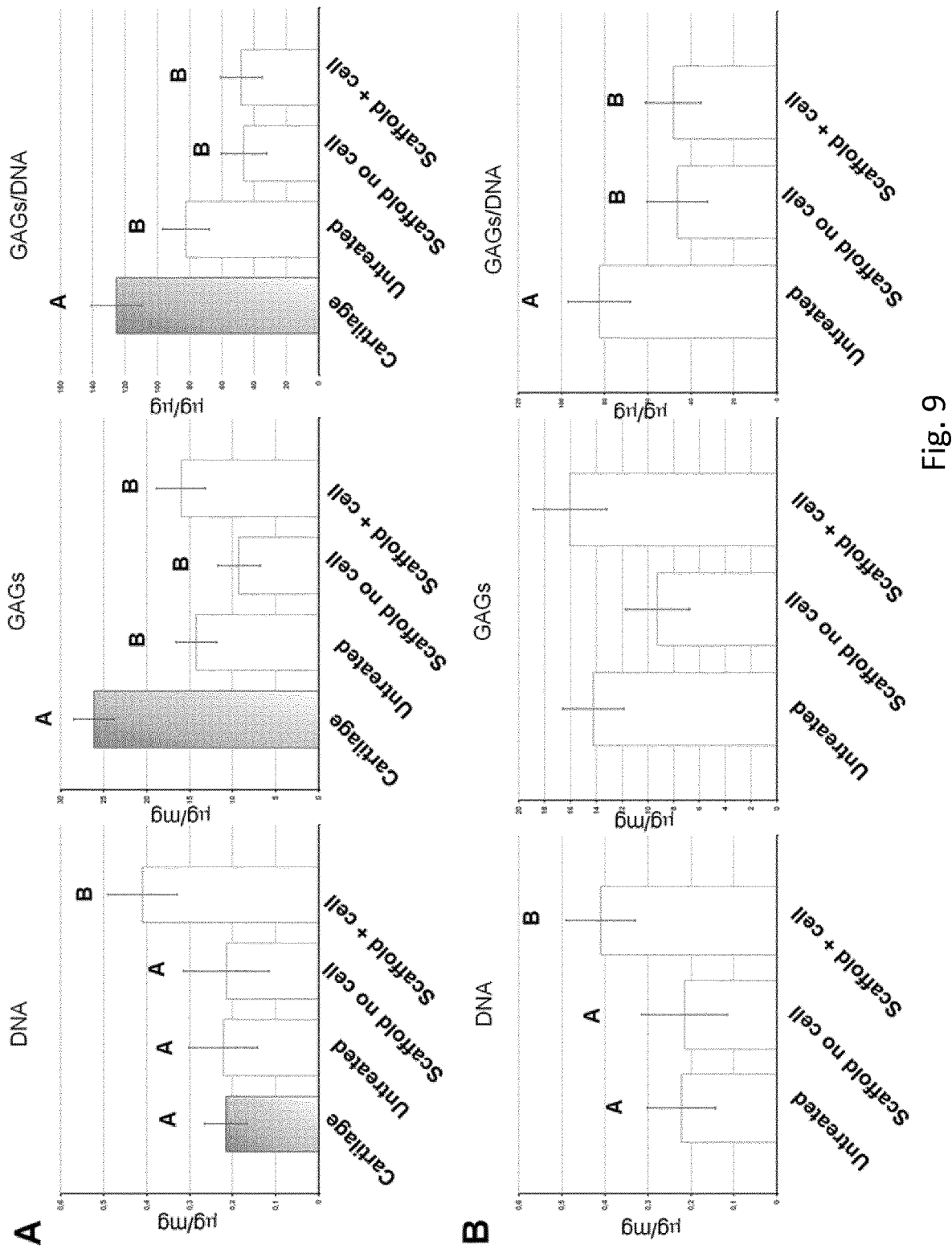

FIG. 9: Biochemical analysis of the repaired lesion: DNA quantification as index of cellularity (μg/mg wet weight); GAGs quantification (μg/mg wet weight); GAGs/DNA ratio (μg/μg). A) Biochemical analysis of the experimental samples with respect to the native cartilage. B) Biochemical analysis of the experimental samples with respect to the different treatments.

Figure 10:
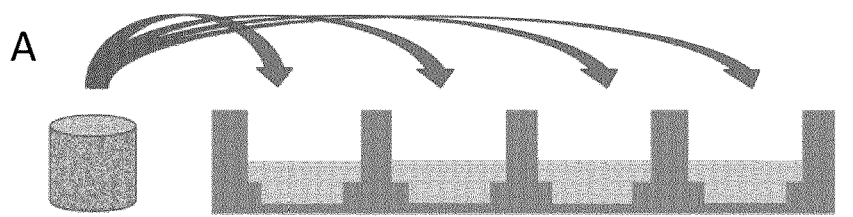
Figure 10:
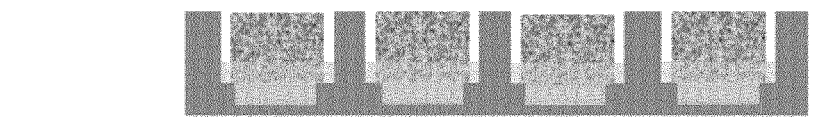
Figure 10:
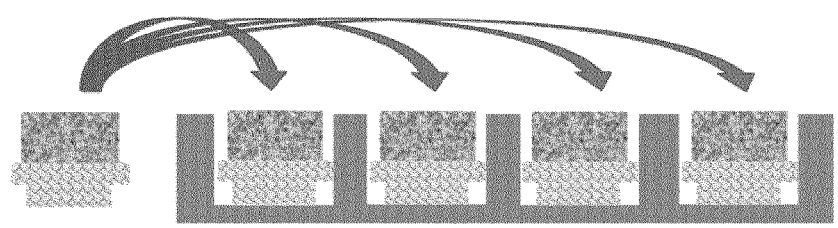
Figure 10:
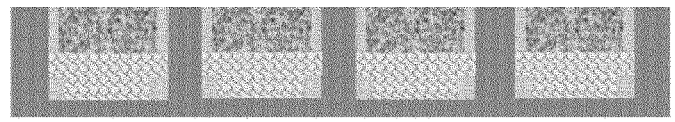
Figure 10:
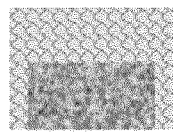
Figure 10:
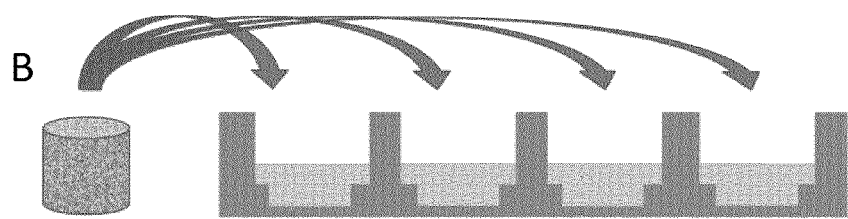
Figure 10:
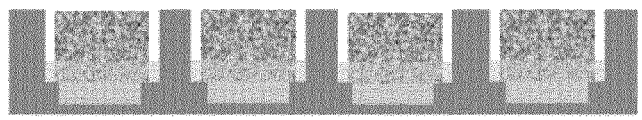
Figure 10:
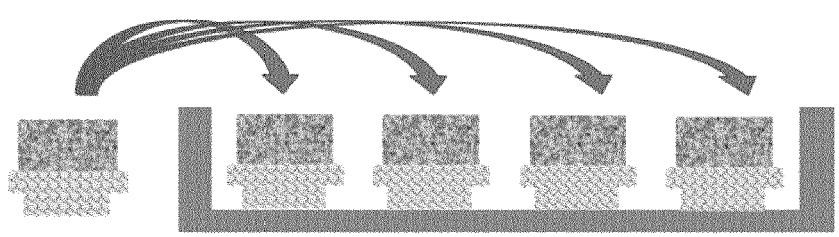
Figure 10:
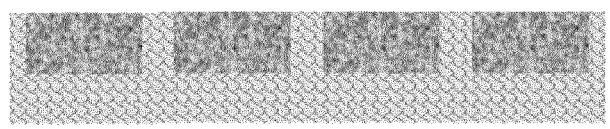
Figure 10:
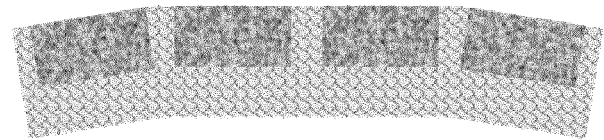
Figure 10:
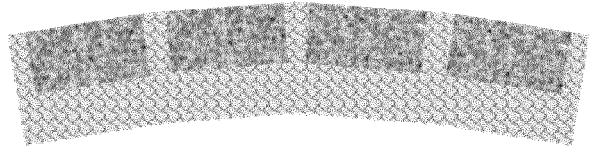
Figure 10:
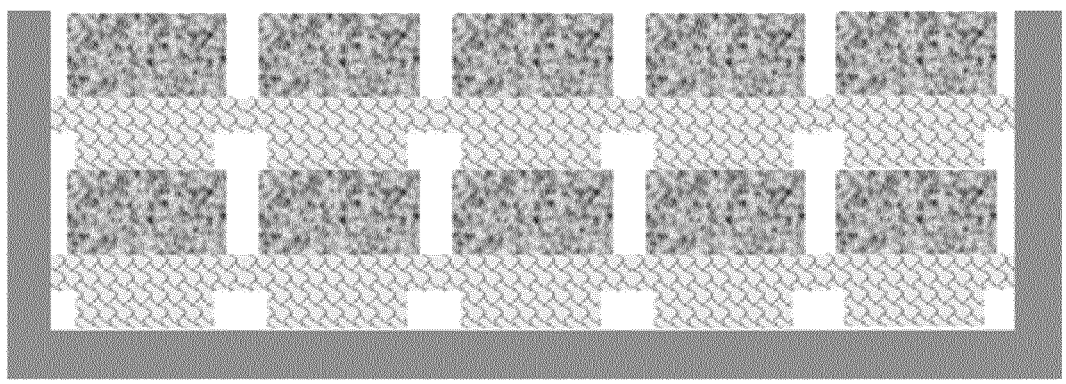
Figure 10:
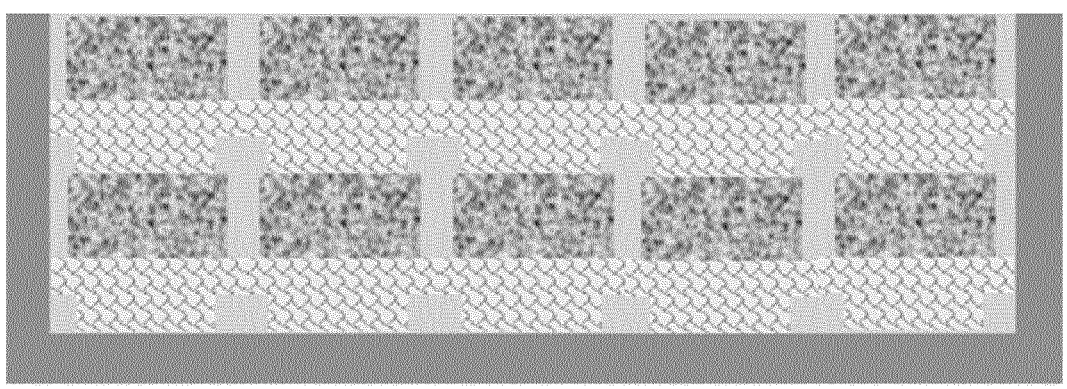
Figure 10:
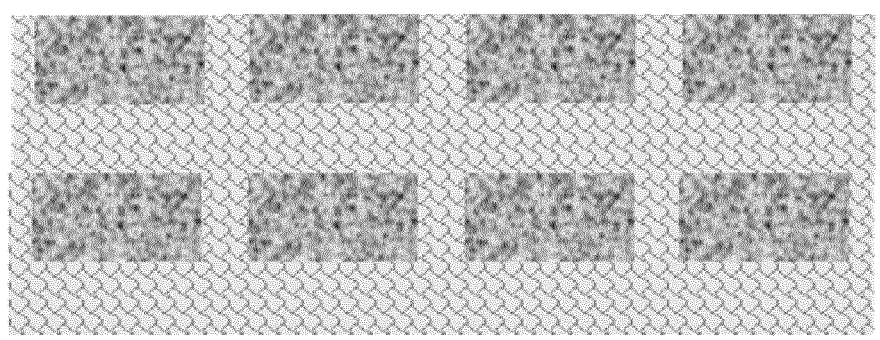
Figure 10:
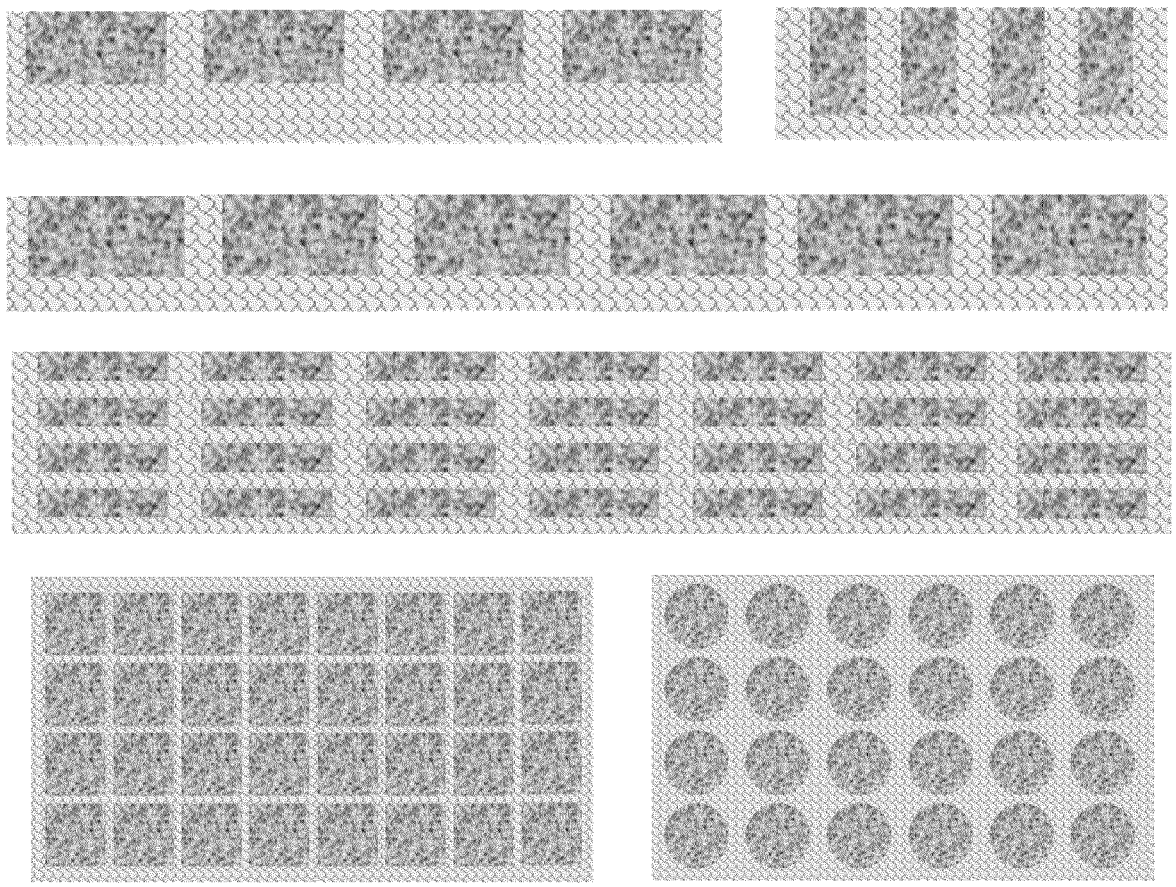
Figure 10:
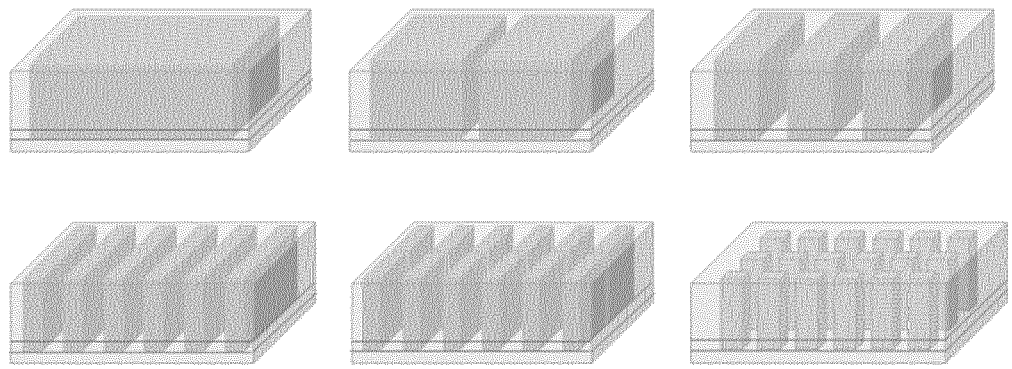

FIG. 10: A schematic representation of the procedure for the osteochondral substitute fabrication, which allows for the obtainment of different complex systems (see text). Different assembling configurations of the bi-layered scaffolds (obtained by Lyo 1) by using different molds B. Mold B for: A) a single bi-layer scaffold; B) a single layer of bi-layered scaffolds; C) two layers of bi-layered scaffolds; D) single and multi-layers of bi-layered scaffolds of different dimensions and shape (circle and squared section). E) The composite scaffolds made of a different number of bi-layered scaffold used, as example, for percentage calculations in Table I.

DETAILED DESCRIPTION OF THE INVENTION

Materials and Methods

Scaffold Fabrication

A novel bilayer scaffold was developed. The scaffold is a three-dimensional structure made of superior collagen scaffold partially penetrating into a bottom hydroxyapatite scaffold. The two fabrication processes of respectively collagen and hydroxyapatite scaffold were separately optimised in previous studies [22]. In order to obtain a partial but strong interconnection between the collagen and hydroxyapatite part of the ostechondral substitute, a multi-step procedure was assessed that is described in the six steps reported below (FIG. 1).

(1) Fabrication of the porous hydroxyapatite cylinders in the suitable dimensions for the in vivo test. Hydroxyapatite macrochanneled porous scaffolds were produced by a polymeric sponge templating method using a reactive submicron powder synthesized by hydroxide precipitation sol-gel route. The HA powder (diameter range 50-200 nanometers) was calcined in air at 900° C. for 60 min before use [23]. The porous hydroxyapatite scaffolds were obtained by impregnating small cylinders (diameter=9.7 mm, height=8.6 mm) of a polyurethane sponge (density of 30 $Kg/m^3$, 25 ppi, kindly provided by ORSA Foam S.P.A. (MTP30TRAU/F1) with a slurry prepared by adding the HA powder (solid load between 50 and 80 wt %) in a polyvinyl alcohol solution (0-3 weight percentage) (Sigma Aldrich, 9002-89-5). Dolapix CE-64 (Zschimmer & Schwarz, Lahnstein, Germany) was used as a dispersant for the impregnation (range 0-1 wt %). Importantly, these values of HA powder, polyvinyl alcohol or dispersant may vary when using different types of HA, from different origin or in case of employment of different type ceramic material in order to obtain a material having similar porous morphology and mechanical characteristics. The infiltrated sponges were then gently squeezed to remove the exceeded slurry, dried for 24 hours in air, heat treated at 500° C. to burnout the sponges and finally sintered between 1200 and 1350° C. The polyurethane sponge dimensions were slightly bigger than the final desired dimensions of the biphasic substitutes in order to compensate the sintering shrinkage.

(2) Fabrication via stereolithografy of a mould (mould A) for the collagen slurry lyophilisation. The mould shape and dimensions are properly designed in order to sustain the hydroxyapatite scaffold and contemporarily to allow for the lyophilisation of the collagen. More in detail, a multiwell plate (7×5) is designed in which every single well is made of two coaxial cylinders of different diameter. The well has a total height of 12 mm ($H_A$) a top diameter of 8.6 mm ($D_A$) and a bottom diameter of 8.2 mm ($d_A$). The height of the part of the well having the smaller diameter (bottom part) is equal to 4 mm ($h_A$). (the dimensions of the mould, the collagen part and the hydroxyapatite parts can vary, depending on the dimensions of the area to be regenerated). An interconnection zone results in which the two materials are co-present for a pre-established height. For the in vivo study here reported the two materials are co-present for 1 mm height (this height can have a variable range; generally, this can be fabricated with a range of 0.5-3 mm). The mould was fabricated in epoxy resin (accuGen 100 HC, 3D System).

(3) Lyophilisation and crosslinking of the collagen scaffolds within the mould A (Lyo 1 and CrossL 1). More in detail, the collagen part was obtained by a freeze drying technique. Briefly, freeze-dried membranes of type 1 equine collagen (Antema®, 911980427, kindly provided by Opocrin S.P.A, Italy) were pulverized in a refrigerate mill and the obtained collagen flakes were suspended in double distilled water in order obtain a collagen concentration of 2 wt %. Importantly, this percentage may vary from 0.5% to 5% when using different types of collagen, from different animal source or from different extraction, in order to obtain a material having similar porous morphology and mechanical characteristics. The slurry was agitated by a magnetic stirrer for two hours and poured into the mould A till a height of 1 mm was reached in the top cylinder of the well ($h_t$). The hydroxyapatite scaffolds from step 1 were then inserted in the mould holes partially filled by collagen slurry. The samples were frozen at −40° C. at 1° C./min and freeze-dried. In order to induce a dehydrothermal (DHT) cross-linking to the collagen fibers, the samples were placed in oven at 110-130° C. under vacuum for a minimum of 48 and a maximum of 96 hours.

(4) Fabrication via stereolithografy of a mould (mould B) for a second collagen lyophilisation. The mould B is designed with the aim of making a perfectly cylinder substitute of the final desired dimensions, covered all around by a very thin layer of collagen. The diameter and the height of the mould B are equal to 9.2 and 12 mm respectively. A thin layer of about 0.3 mm will result. The dimension of this thin layer of collagen around the material may vary if need, based on particular surgical condition; generally it may range from 0.1 to 2 mm. In fact, the collagen layer has the double purpose of eliminating the small step derived from the use of the mould A and facilitating the substitute insertion in the ostechondral lesion by the medical staff.

(5) Lyophilisation and crosslinking of the collagen scaffolds within the mould B (Lyo 2 and CrossL 2). The biphasic substitutes from step 3 were inserted in the mould B holes, then covered all around by collagen slurry. In this case, the collagen slurry was added till the well was completely filled. The samples were frozen at −40° C. at 1° C./min and freeze-dried again (Lyo 2). A dehydrothermal (DHT) cross-linking treatment (CrossL 2) was applied to the samples using the same conditions of CrossL 1.

(6) Substitutes sterilization in oven under vacuum at 160° C. for 2-4 hours.

Chondrocyte Isolation, Expansion and Seeding

Approval for the study was obtained from the Italian Ministry of Health.

Six four-months old Landrance large white pigs were used for this study. All animals were anesthetized as follows: Telazol 100 mg/ml (Tiletamine HCl 50 mg/ml and Zolazepam HCl 50 mg/ml; Fort Dodge Animal Health, Fort Dodge, Iowa, USA) at the dosage of 1.4 mg/Kg; Xylazine HCl 100 mg/ml (Boehringer Ingelheim Vetmedica, Inc. St. Joseph, Mo., USA) at the dosage of 2.0 mg/Kg; Robinul-V 0.2 mg/ml (Glycopyrrolate; Fort Dodge Animal Health) at the dosage of 0.01 mg/Kg. After induction, anesthesia was maintained with Isoflurane (Baxter Healthcare Corporation, Deerfield, Ill., USA). The animals were then placed in the supine position. A longitudinal paramedian incision was made in the medial aspect of the right knee. The vastus medialis muscle, which completely surrounds the patella in the pig, was sectioned to expose the articular capsule. A capsulotomy was performed and the patella was dislocated laterally to expose the articular surface of the trochlear groove. Six cartilage lesions measuring 6 millimeter in diameter (chondral plugs) and extending up to the border with the calcified cartilage were produced in the medial aspect of the patellar groove with a standardized core punch (FIG. 2A). The chondral plugs were placed in 50 ml test tubes containing phosphate buffered saline and the antibiotic/antimycotic solution. The wound was then closed in layers in standard fashion. An impermeable dressing using betadine gel was applied (Viatris spa, Milan, Italy). Prophylactic antibiotic therapy was instituted using 1,200 units of penicillin G (Bicillin L-A; Wyeth Laboratories Inc. Philadelphia, Pa., USA), given on days two and four postoperatively. Pain management consisted of Duragesic 75 μg/h (Fentanyl transdermal system; Janssen Pharmaceutica Inc. Titusville, N.J., USA) and 0.3 mg of buprenorphine (Buprenex injectable; Reckitt & Colman Pharmaceuticals Inc. Richmond, Va., USA). No immobilization was applied after operation and the animal was allowed to move freely.

Some cartilage slices ("native cartilage") harvested from the same animals were frozen as a control tissue for biochemical analysis; all other cartilage slices were digested in Ham's medium (Celbio, Pero, Mich., Italy) containing 0.1% collagenase Type 2 (DBA-Italia Srl, Segrate, Mich., Italy) and 1% of the antibiotic/antimycotic solution (10,000 units Penicillin, 10 mg Streptomycin and 25 μg Amphotericin B/ml in 0.9% sodium chloride; Sigma Chemical Co., St. Louis, Mo., USA). The specimens were incubated overnight in an oscillating water bath at 37° Celsius. Undigested tissue and debris were removed by filtering the cell suspension using a 100 micron sterile filter (BD Falcon, Bedford, Mass., USA). The cell suspension obtained was centrifuged at 1400 rpm for 10 minutes. The cell pellet was washed twice in phosphate buffered saline (Celbio) and 2% antibiotic/antimycotic solution. Viability of the chondrocytes was assessed by Trypan blue staining (Sigma) and recorded as a percentage of viable chondrocytes per high power field. The exact cell count per milliliter was established using a haemocytometer. Fresh chondrocytes were plated at a concentration of 10000 cells/cm$^2$ and cultured in DMEM (Lonza, Italia) containing 10% FBS (Euroclone), 1% glutamine (Euro-Clone, Milan, Italy), and 1% antibiotic/antimycotic solution (Sigma), 5 ng/ml FGF-2 (R&D Systems, Minneapolis, Minn., USA), 10 ng/ml TGFβ-1 (R&D Systems, Minneapolis, Minn., USA); medium was changed three times a week. After two passages, the de-differentiated chondrocytes were collected, resuspended in a solution containing bovine fibrinogen (for example 110 mg/ml, FlukaChemie GmbH, Buchs, SG, Switzerland), aprotinin (0.2 mg/ml) (Sigma), tranexamic acid (1.5 mg/ml) (Sigma) and adjusted to a concentration of 80×10$^6$ cells/ml. Then, 100 μl of the fibrinogen-cell suspension was seeded onto the scaffold on the collagen layer (8×10$^6$ cells/scaffold; possible range: 0.5-16×10$^6$ cells/scaffold) prepared according to the design parameters optimized previously [24]. After complete cell absorption, 100 μl of thrombin (1.37 mg/ml, Chemicon International, Inc., Temecula, Calif., USA) were added in order to form fibrin glue. After 30 minutes, complete polymerization was reached and the scaffolds were placed in culture flasks for the in vitro culture. The seeded scaffolds were cultured in vitro for 3 weeks in DMEM (Lonza, Italia) containing 10% FBS (Euroclone), 1% glutamine (Euro-Clone, Milan, Italy), and 1% antibiotic/antimycotic solution (Sigma), ascorbic acid 50 μg/ml (Sigma), 10 ng/ml TGFβ-3 (R&D Systems, Minneapolis, Minn., USA); medium was changed three times a week (FIG. 2B).

Study Design

Animals were anesthetized and positioned as previously described. A longitudinal paramedian incision was made in the medial aspect of the right knee, on the previous skin scar and duplicating the prior surgical approach. Articular capsule was open and the previously sites of cartilage harvest were identified. The repairing tissue formed in the six chondral lesions was removed and six new osteochondral lesions encircling the previous defect areas were performed with a standardized core punch measuring 8 millimeter in diameter and 9 mm in depth. Three different types of treatment were tested a) implants of bilayer scaffolds seeded with autologous chondrocytes (group cell +); b) implants of osteochondral substitute unseeded (group cell −); no implants (untreated group). Each animal was treated with two seeded bilayer scaffolds and two unseeded bilayer scaffolds; two lesions per animal were left untreated (FIG. 2C). Care was taken in randomizing treatment to all six experimental lesion sites (proximal, intermediate and distal on the medial and lateral aspects of the patellar groove). This was done to avoid influencing the reparative process from the different anatomical locations of the lesions in the patellar groove of the animal knees. The capsule was then closed and the wound was sutured in layers. Post-operative care, medications, and dressings were as previously described. The animals were able to stand on the operated leg and allowed to walk freely. Generally, all animals were able to stand and bear full weight on four legs after 24-72 hours postoperatively. Twelve weeks after implantation all animals were euthanized using an overdose of Pentobarbital (100 mg/kg IV), the knee joints opened and the repaired tissue evaluated as described below.

Tissue Repair Evaluation

Gross Evaluation

After the opening of the joints the macroscopic appearance of the repaired tissue was examined using the ICRS Macroscopic Score [25], which evaluates the degree of defect repair, the integration to the border zone, and the macroscopic appearance. Two observers, both blind to the treatment, independently scored the specimens.

Histochemical Analysis

The repair areas were removed with healthy tissue surrounding the lesions. Each sample was cut in half, along the central axis of the lesions. Half sample was fixed in 10% (v/v) phosphate-buffered formaldehyde. The samples were then dehydrated in a graded 50% (v/v), 70% (v/v), 95% (v/v) and 100% (v/v) ethanol series, embedded in paraffin and cut into 4 μm-thick sections. Finally, the sections were stained with SAFRANIN-0, using a standard staining protocol, for the evaluation of the morphology and GAGs deposition. Some sections were used for immunohistochemical analysis of collagen type I and II (Chondrex staining kit, Chondrex Inc, USA). After rehydration, heat-induced antigen retrieval was performed by treating the sections in citrate buffer, pH 6.0, in a microwave oven. Sections were then washed 3 times in PBS (pH 7.4). Before immunostaining, sections were treated in a 2% hyaluronidase solution (Sigma) at room temperature for 30 min. In order to block endogenous peroxidase activity, the sections were incubated in an aqueous solution of 1% $H_2O_2$ for 30 min at room temperature and then washed 3 times in PBS. Sections were incubated overnight with mouse anti-collagen type II antibody (Chondrex, Inc; 1:500). Labeled biotin secondary antibody-streptavidine peroxidase (1:500) was applied for 1 hour at room temperature. Peroxidase activity was visualized with diaminobenzidine (DAB; Dakocytomation, Milan, Italy) and $H_2O_2$ as substrates. All incubations were performed in a moist chamber at room temperature, using PBS for washes between incubation steps. Sections were counterstained with hematoxylin, dehydrated and mounted in mounting medium. Photomicrographs were taken with an Olympus BX51 microscope (Olympus, Italy) equipped with a digital camera and final magnifications were calculated. The experimental samples stained for SAFRANIN-O were analyzed at the optical microscope in order to evaluate the parameters established by ICRS II: each criterion was evaluated based on the visual analog scale and graded from 0 to 100 [26]. The obtained values were analyzed in order to highlight the statistically significant differences among the three experimental groups.

Biochemical Analyses

The biochemical analysis was performed on the other half of samples for each experimental condition (1 seeded scaffold, 1 unseeded scaffold and 1 untreated lesion). The samples were digested in papain (Sigma) for 16-24 h at 60° C.; the digestion solution was composed of 125 μg/mL of papain (Sigma) in 100 mM sodium phosphate, 10 mM sodium EDTA (Sigma), 10 mM cysteine hydrochloride (Sigma), 5 mM EDTA adjusted to pH 6.5 and brought to 100 mL of solution with distilled water. After the digestion, the samples were stored at −80° C. until analysis. Aliquots of the digested samples were assayed separately for proteoglycan and DNA contents. Proteoglycan content was estimated by quantifying the amount of sulphated glycosaminoglycans using the 1,9-dimethylmethylene (DMB) blue dye binding assay (Polysciences Inc., Washington, Pa., USA) and a microplate reader (wavelength: 540 nm). The standard curve for the analysis was generated by using bovine trachea chondroitin sulfate A (Sigma). DNA content was evaluated with the Quant-iT Picogreen dsDNA Assay Kit (Molecular Probes, Invitrogen, Eugene, Oreg., USA) and a fluorescence microplate reader and standard fluorescein wavelengths (ex-citation 485 nm, emission 538 nm, cut-off 530 nm). The standard curve for the analysis was generated using the bacteriophage lambda DNA supplied with the kit.

Statistical Analysis

Descriptive statistics were used to determine groups' means and standard deviations for numerical data, and analysis was performed using analysis of variance. Statistical significance was defined as a p-value of <0.05.

Results

Fabrication of the Substitute

The collagen/hydroxyapatite substitutes were properly fabricated. In FIG. 3 pictures of bilayered scaffolds after first lyophilisation (a), after integration between the collagen and the hydroxyapatite layers (b) at the end of the fabrication process before the implant in the animal (c), are reported.

Morphology and Scoring of the Repaired Lesions

At the gross evaluation of specimens, all grafts were still in their original location. The ICRS macroscopic score was significantly lower in the cell + group when compared with cell − and untreated group (p<0.05 and p<0.005, respectively). No statistically significant difference was detected between cell − and untreated group (FIG. 4). The obtained data demonstrate a more efficient repair in the untreated lesions and in the lesions treated with the scaffold alone, suggesting a strong contribute of endogenous bone marrow cells in the regeneration of the osteochondral lesion. Such endogenous contribute was reduced in the seeded scaffolds probably as a consequence of the chondral collagen phase where autologous chondrocytes had been seeded with fibrin glue and they had already produced a matrix network at the moment of the implantation, leading to a less efficient colonization of the chondral phase. Histological evaluation showed the presence of a newly formed repair tissue, with areas of fibroblast-like tissue and areas of hyaline-like tissue in all groups. The three different experimental groups showed significant differences in scores only in two parameters; in particular, the unseeded osteochondral scaffolds showed higher values (P<0.05) for cell morphology and for the surface/superficial assessment, with respect to both the seeded scaffolds and the untreated lesions (FIG. 5). As demonstrated by the histochemical analysis with SAFRANIN-O, the unseeded scaffolds were characterized by a linear superficial layer with an uniform GAGs distribution throughout the lesion site (FIG. 6A); moreover, the cells were chondrocytes-like and some of them were surrounded by lacunae (FIG. 7A,D). The seeded scaffolds and the repairing tissue of the untreated lesions showed irregular superficial layers with hollows (FIG. 6B,C); in the superficial layer, the cell morphology is mainly fibroblast-like with no lacunae (FIG. 7B,C), while in the deeper region some cells showed a chondrocyte-like phenotype, but no lacunae were present around them (FIG. 7E,F). Immunohistochemical analysis for collagen type 2 showed in the untreated group a scarce immunoreactivity, while in the cell – group a high reactivity in the lateral part of the defect was observed; additionally, in the cells + group an increasing immunopositivity from the superficial to the deep level of the defect was also detected. The evaluation of collagen type 1 showed in all groups a scarce immunopositivity that becomes stronger in a deep level of the defect only in the cell + group (FIG. 8).

Biochemical Analysis of the Repaired Lesions

The experimental samples were digested in papain in order to measure either the DNA content, an index of cellularity, or GAGs production as a marker of the extracellular matrix. With respect to native cartilage, only the seeded osteochondral scaffolds showed a significative ($P<0.05$) higher cellularity (FIG. 9A) while GAGs production and GAGs/DNA ratio were lower ($P<0.05$) in all the experimental groups.

Comparing the different experimental groups, the seeded scaffolds showed a significative higher cellularity while the GAGs/DNA ratio was higher in the untreated lesions with respect to the seeded and unseeded scaffolds ($P<0.05$); no differences were observed in GAGs production among the different experimental groups (FIG. 9B).

DISCUSSION

In the present invention, a novel three-dimensional biphasic substitute made of an organic/inorganic hybrid material was developed. The scaffold is preferably made of the combination of a collagen type 1 sponge, previously characterized for its compatibility and application as a supporting materials for cartilage tissue engineering applications, and a HA component. The bilayer scaffold was successfully produced thanks to the fabrication of a properly designed mould via stereolithography that allowed for obtaining an interconnection zone where the two materials (collagen and HA) were co-present for a pre-established thickness (FIG. 1). In particular, for the in vivo study here reported the two materials are co-present for 1 mm height, but this height can have a variable range: generally, this can be fabricated with a range of 0.5-3 mm. This particular structure has the advantage of allowing for a greater integration of the two materials and also, duplicating the native tissues, disposing the ideal substratum for a proper re-population following in vivo implantation. Additionally, the second novelty introduced, i.e. the fabrication via stereolithografy of a second mould for a further collagen lyophilisation around the HA cylinder, has the double aim of both improving the collagen/hydroxyapatite integration and facilitating the substitute insertion in the osteochondral lesion, allowing for a certain degree of change in the diameter of the cylinder through a different hydration. Osteochondral defects created in the surface of the trochlea of adult pigs were treated by implanting a biphasic scaffold, which were either seeded with autologous chondrocytes or left unseeded. The use of collagen type 1 sponges has been already introduced by several groups for the in vitro engineering of cartilage [27-30] demonstrating that this biocompatible material can support chondrocytes survival and synthetic activity during time with the consequent maturation of the scaffold into a chondral substitute. Some works introduced the combination of fibrin glue to ameliorate scaffold seeding and maturation [31,32]; in particular, Malicev et al. combined fibrin glue with collagen type 1 sponge improving scaffold seeding and the in vitro maturation [33]. The bone phase was left unseeded allowing the mesenchymal stem cells from the adjacent bone marrow to migrate following the implantation and undergo an osteogenic differentiation.

The overall results of the authors' study, at 3 months follow-up, showed a certain discrepancy between macroscopic and histological scores. In particular, the ICRS macroscopic score was significantly lower in the cell + group when compared with cell – and untreated group; so, at early repair time, the use of chondrocytes did not seem to provide an advantage over the use of a scaffold alone. The intrinsic limit of Macroscopic analysis is related to the superficial evaluation of the sample wherein the results are obtained by examining the external aspects of the samples. Thus, the differences in the results evaluated with Macroscopic analysis and histological analysis are due to the different characteristics of the two methodology approaches. Moreover, at the histological evaluation, the repair induced by the acellular scaffold was better regarding the histological aspect of the superficial layer and the morphology of cells, demonstrating that the scaffold was able to allow the colonization and the maturation of the cells deriving from the local sources. So, the structure of the scaffolds permitted the migration of stem cells and their subsequently chondrogenic differentiation. The authors cannot exclude, however, the contribution of other cells deriving from blood or from the surrounding tissues, which were able to differentiate into a cartilaginous or fibrocartilaginous phenotype in the joint environment. The scaffold seeded with autologous chondrocytes promoted the formation of a repairing tissue with high cellularity but low GAGs production, suggesting a low chondrocytes activity. So, at the experimental time of this study, the quantity and the quality of the repaired tissue was far to be similar to the native cartilage. However, the immunohistochemical analysis revealed in the cells + group an increasing immunopositivity for the collagen type 2 from the superficial to the deep level of the defect, showing a more hyaline aspect of the repaired tissue, compared with the others groups.

In conclusion, this study showed that the bilayer scaffold of the present invention is easy to handle for surgical implant and stable in the implant site; at the end of experimental time, no signs of synovitis were revealed and all implants were well integrated to the surrounding tissue. The quality of the repaired tissue produced within the bulk of the unseeded osteochondral scaffolds demonstrated the potential of this material for one-step procedure for articular cartilage repair.

REFERENCES

1. Pan J, et al. J Orthop Res. 2009 October; 27(10):1347-52
2. Mente P L, Lewis J L. J Orthop Res. 1994 September; 12(5):637-47.
3. Madry H, et al. Knee Surg Sports Traumatol Arthrosc. 2010 April; 18(4):419-33.
4. Westacott C. J Musculoskelet Neuronal Interact. 2002 December; 2(6):507-9.
5. Lories R J, Luyten F P. Nat Rev Rheumatol. 2011 January; 7(1):43-9.
6. Ding M. ActaOrthop Suppl. 2010 February; 81(340):1-53
7. Bijlsma J W, Berenbaum F, Lafeber F P. Lancet. 2011 Jun. 18; 377(9783):2115-26
8. Sellam J, Berenbaum F. Nat Rev. Rheumatol. 2010 November; 6(11):625-35.
9. Intema F, et al. 2010 May; 18(5):691-8.
10. Intema F, et al. J Bone Miner Res. 2010 July; 25(7):1650-7
11. Mitchell N, Shepard N. J Bone Joint Surg Am. 1976 March; 58(2):230-3

12. Steadman J R, et al. Orthopade. 1999 January; 28(1): 26-32. German.
13. Hangody L, et al. Orthopedics. 1998 July; 21(7):751-6.
14. J. S. Temenoff, A. G. Mikos. Biomaterials, 21 (2000) 431-440.
15. D. Schaefer et al. Arthritis Rheum., 46 (2002) 2524-253.
16. A. Tampieri, et al. Biomaterials, 29 (2008) 3539-46.
17. Gun-II I, et al., Tissue Engineering 2010 16 (4):1189-1201.
18. Maehara H, et al. J Orthop Res. 2010 May; 28(5):677-86.
19. J. M. Oliveira, et al. Biomaterials, 27 (2006) 6123-37.
20. Xue D, et al. J Biomed Mater Res A. 2010 July; 94(1):259-70.
21. Qu D, et al. J Biomed Mater Res B Appl Biomater. 2011 January; 96(1):9-15.
22. Gervaso F, et al. Key Engineering Materials, Vols. 493-494, pp 890-895, 2012)
23. Gervaso F, et al. Int. J. Appl. Ceram. Technol., 9 [3] 507-516 (2012)
24. Deponti D, et al. Tissue Eng Part A, June; 18(11-12): 1109-22, 2012,
25. van den Borne M. P. J. et al. Osteoarthritis and Cartilage 2007 Dec. 15(12) 1397-402
26. Mainil-Varlet P, et al. Am J Sports Med. 2010 May; 38(5):880-90.
27. Roche S et al. Biomaterials. 2001 January; 22(1):9-18.
28. Lu H, Ko Y G, Kawazoe N, Chen G. Biomaterials. 2010 August; 31(22):5825-35.
29. Oliveira S M, et al. J Biomed Mater Res A. 2010 August; 94(2):371-9.
30. Mizuno S, Allemann F, Glowacki J. J Biomed Mater Res. 2001 Sep. 5; 56(3):368-75.
31. Wang W, et al. Biomaterials. 2010 August; 31(23):5953-65.
32. Chou C H, et al. J Biomed Mater Res A. 2007 Sep. 1; 82(3):757-67.
33. Malicev E et al. Biotechnol Bioeng. 2007 Feb. 1; 96(2):364-70.

The invention claimed is:

1. A synthetic composite material for tissue repair comprising:
a first sponge layer formed from an organic material optionally complexed with at least one polyanionic substance, said first sponge layer having side walls, and said first sponge layer being optionally seeded with cells;
a second porous layer abutting said first sponge layer, said second porous layer formed from an inorganic material, and said second porous layer having side walls; and
a third layer abutting and covering said side walls of said first sponge layer and said side walls of said second porous layer, said third layer formed from said organic material of said first sponge layer;
wherein said first sponge layer and said second porous layer are joined at said abutment and define an interconnection zone:
wherein said interconnection zone comprises said organic material of said first sponge layer penetrating and filling the pores of said inorganic material of said second porous layer for a distance extending past said abutment resulting in a mixture of said organic material and the inorganic material being co-present in said interconnection zone, said distance extending past said abutment up to 3 mm into said second porous layer; and
wherein said first sponge layer and said second porous layer each have an exposed surface most distal from said abutment.

2. The synthetic composite material according to claim 1, wherein said first layer has a thickness of 0.1-20 mm, said second layer has a thickness of 2-400 mm, said third layer has a thickness of 0.1-2 mm high, said interconnection zone has a thickness of 0.5-3 mm.

3. The synthetic composite material according to claim 1, wherein the organic material is selected from the group consisting of at least one collagen and derivatives thereof, chondroitin-sulphate, hyaluronic acid and derivatives thereof, polyglactin, polydioxanone, alginate, agarose, chitosan and derivatives thereof, fibrin glue, polyethylene glycol diacrylate, or a combination thereof.

4. The synthetic composite material according to claim 1, wherein the inorganic material is selected from the group consisting of hydroxyapatite, calcium sulphate, calcium silicate, calcium phosphate, magnesium silicate, metal or a combination thereof.

5. The synthetic composite material according to claim 1, wherein the second porous layer has a pore dimension between 50 um and 700 um.

6. The synthetic composite material according to claim 1, wherein the organic material of the first layer is complexed with said at least one polyanionic substance.

7. The synthetic composite material according to claim 1, wherein the first layer is seeded with said cells.

8. The synthetic composite material according to claim 7, wherein said cells are chondrocytes.

9. A composite structure comprising one or more synthetic composite material according to claim 1.

10. A synthetic bone material, bone implant, bone graft, bone substitute, bone scaffold, filler, coating or cement comprising the synthetic composite material according to claim 1.

11. A synthetic skin material, plaster, bandage comprising the synthetic composite material according to claim 1.

12. The synthetic composite material according to claim 6, wherein the metal is magnesium or titanium.

13. The synthetic composite material according to claim 1, wherein the inorganic material is hydroxyapatite.

14. The synthetic composite material according to claim 1, wherein said synthetic composite material has a percentage by volume of 46 to 72 percent for said first layer, 19 to 36 percent for said second layer, and 9 to 18 percent for said interconnection zone.

15. The synthetic composite material according to claim 9, wherein said at least one polyanionic substance is a signaling molecule.

16. The synthetic composite material according to claim 1, wherein said signaling molecule is a growth factor selected from the group consisting of transforming growth factor-β1, bone morphogenetic proteins and insulin growth factor-1.

17. A method of treatment of osteochondral defects comprising implanting in a subject in need thereof the synthetic composite material according to claim 1.

18. A method of treatment of skin defects comprising applying on a subject's skin in need thereof the synthetic composite material according to claim 1.

* * * * *